(12) United States Patent
Kono et al.

(10) Patent No.: US 10,120,181 B2
(45) Date of Patent: Nov. 6, 2018

(54) OPTICAL UNIT AND ENDOSCOPE

(71) Applicant: OLYMPUS CORPORATION, Tokyo (JP)

(72) Inventors: Shinya Kono, Tokyo (JP); Takehiko Iguchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 184 days.

(21) Appl. No.: 15/228,601

(22) Filed: Aug. 4, 2016

(65) Prior Publication Data

US 2016/0341950 A1  Nov. 24, 2016

Related U.S. Application Data

(63) Continuation of application No. PCT/JP2014/072902, filed on Sep. 1, 2014.

(30) Foreign Application Priority Data

Feb. 6, 2014 (JP) .................. 2014-021186

(51) Int. Cl.
  *G02B 15/14*   (2006.01)
  *G02B 23/24*   (2006.01)
  *G02B 7/04*    (2006.01)
  *G02B 7/08*    (2006.01)
  *G02B 23/26*   (2006.01)
  (Continued)

(52) U.S. Cl.
  CPC ...... *G02B 23/2438* (2013.01); *A61B 1/00096* (2013.01); *A61B 1/00188* (2013.01); *G02B 7/04* (2013.01); *G02B 7/08* (2013.01); *G02B 7/102* (2013.01); *G02B 23/26* (2013.01);

*H02K 41/0356* (2013.01); *H04N 5/2256* (2013.01); *H04N 2005/2255* (2013.01)

(58) Field of Classification Search
  CPC .... G02B 23/2438; G02B 7/102; G02B 23/26; G02B 7/08; G02B 7/04
  See application file for complete search history.

(56) References Cited

U.S. PATENT DOCUMENTS

| 5,876,327 A | 3/1999 | Tsuyuki et al. |
| 2013/0314517 A1* | 11/2013 | Makiyama ............. A61B 1/045 348/65 |

FOREIGN PATENT DOCUMENTS

| JP | S63-163310 A | 7/1988 |
| JP | 2-301023 A | 12/1990 |

(Continued)

OTHER PUBLICATIONS

International Search Report issued in PCT/JP2014/072902 dated Dec. 2, 2014 (in English and Japanese).

(Continued)

*Primary Examiner* — Joseph P Martinez
(74) *Attorney, Agent, or Firm* — Scully, Scott, Murphy & Presser, P.C.

(57) ABSTRACT

The optical unit is including a tubular fixed part, a front frame part, a back frame part, a movable part, and a voice coil motor that is capable of moving the movable part relatively with respect to the fixed part in a direction of the axis by a coil located in the fixed part and a magnet located in the movable part and magnetically polarized in a direction orthogonal to the axis, wherein at least a part of the movable part is included in a portion of the front frame part projected in the axis direction.

12 Claims, 15 Drawing Sheets

(51) Int. Cl.
*H02K 41/035* (2006.01)
*A61B 1/00* (2006.01)
*G02B 7/10* (2006.01)
*H04N 5/225* (2006.01)

(56) References Cited

FOREIGN PATENT DOCUMENTS

| | | |
|---|---|---|
| JP | 5-196850 A | 8/1993 |
| JP | 8-15593 A | 1/1996 |
| JP | 8-86949 A | 4/1996 |
| JP | 10-133126 A | 5/1998 |
| JP | 3142643 U | 5/2008 |
| JP | 2009-160276 A | 7/2009 |
| JP | 2010-243195 A | 10/2010 |
| WO | 2013/054787 A1 | 4/2013 |

OTHER PUBLICATIONS

Zhengjun, G., "Magnetic Compass Technology—How Fluxgate works", May 31, 2003, pp. 132-134.

* cited by examiner

OPTICAL UNIT AND ENDOSCOPE

CROSS-REFERENCE TO RELATED APPLICATIONS

This application is a continuation claiming priority on the basis of Japan Patent Application No. 2014-021186 applied in Japan on Feb. 6, 2014 and based on PCT/JP2014/072902 filed on Sep. 1, 2014. The contents of both the PCT application and the Japan Application are incorporated herein by reference.

BACKGROUND OF THE INVENTION AND RELATED ART STATEMENT

The present invention relates to an optical unit and an endoscope, in which a voice coil motor is used to drive a movable part for advanceable and retractable movement.

So far, there has been an endoscope disclosed in the prior art, which includes a moving lens frame provided with a moving lens and has a zoom function of varying taking magnification by retractable movement of the moving lens frame (see JP(A) 2010-243195).

SUMMARY OF INVENTION

According to a certain aspect of the invention, there is an optical unit provided, which is including a tubular fixed part with a given axis as center, a front frame part that holds a front lens group in place and is attached to the object side of the fixed part with the axis as center, a back frame part that holds a back lens group in place and is attached to the image side of the fixed part with the axis as center, a movable part that holds a moving lens group in place and is located inside the fixed part with the axis as center, and a voice coil motor that is capable of moving the movable part relatively with respect to the fixed part in a direction of the axis by a coil located in the fixed part and a magnet located in the movable part and magnetically polarized in a direction orthogonal to the axis, wherein at least a part of the movable part is included in a portion of the front frame part projected in the axis direction.

According to a certain aspect of the invention, there is an endoscope provided, which is including the aforesaid optical unit.

DESCRIPTION OF EMBODIMENTS

The optical unit according to the embodiment described herein is now explained.

Figure 1:
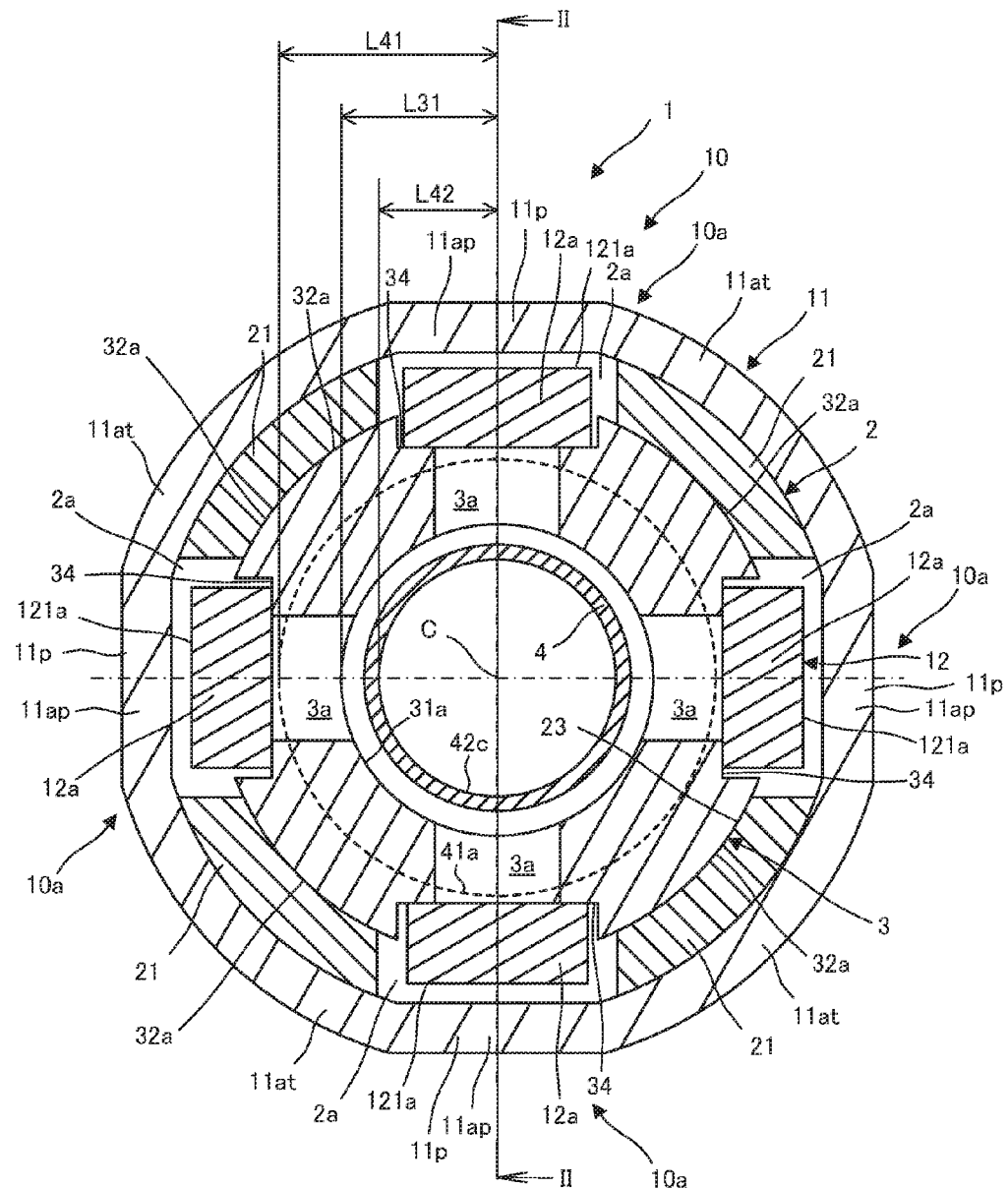
FIG. 1 is a sectional view of the optical unit according to the first embodiment of the invention as taken orthogonally with respect to its axis.
Figure 2:
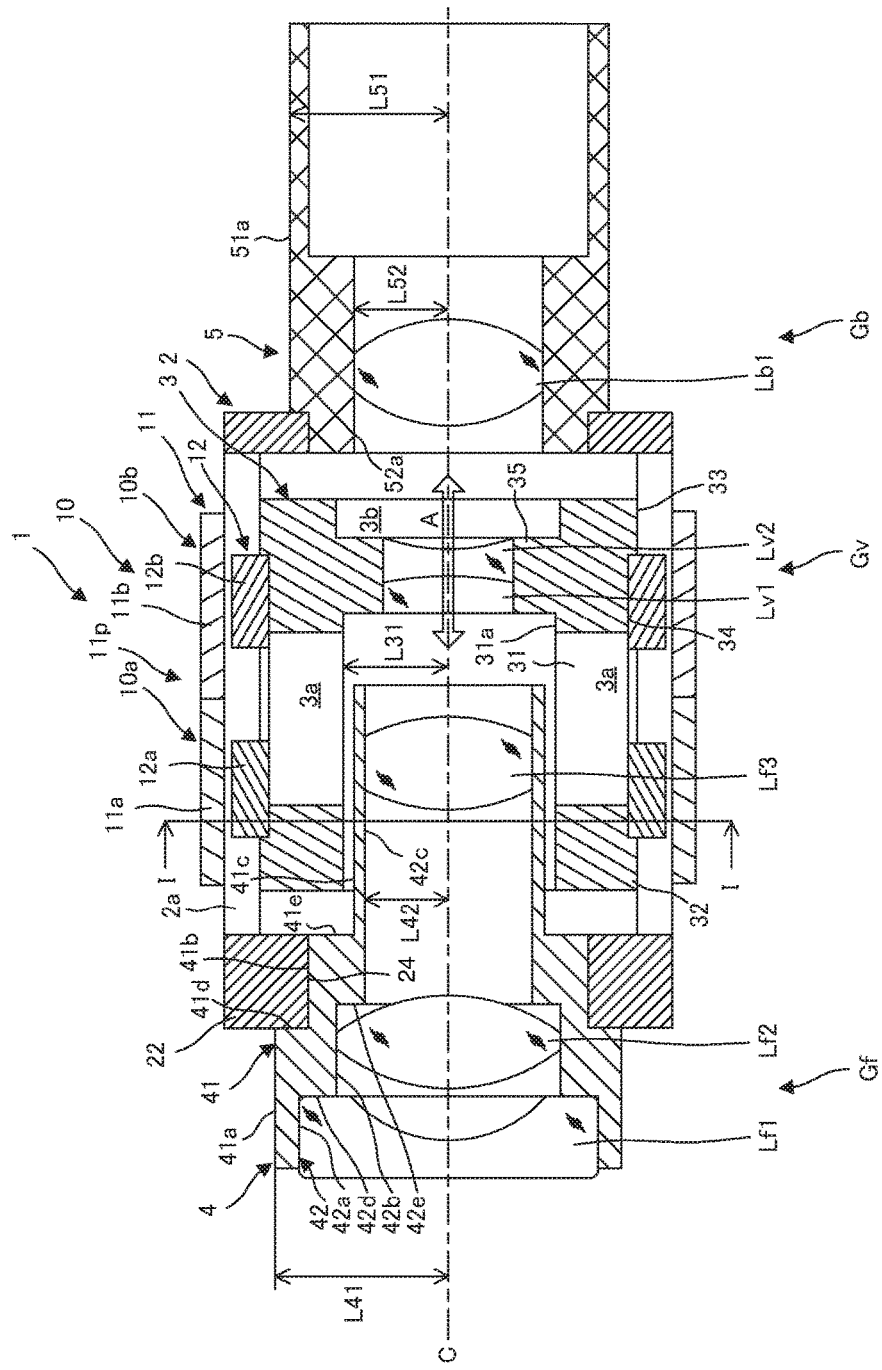
FIG. 2 is a sectional view of the optical unit according to the first embodiment including its axis.
Figure 3:
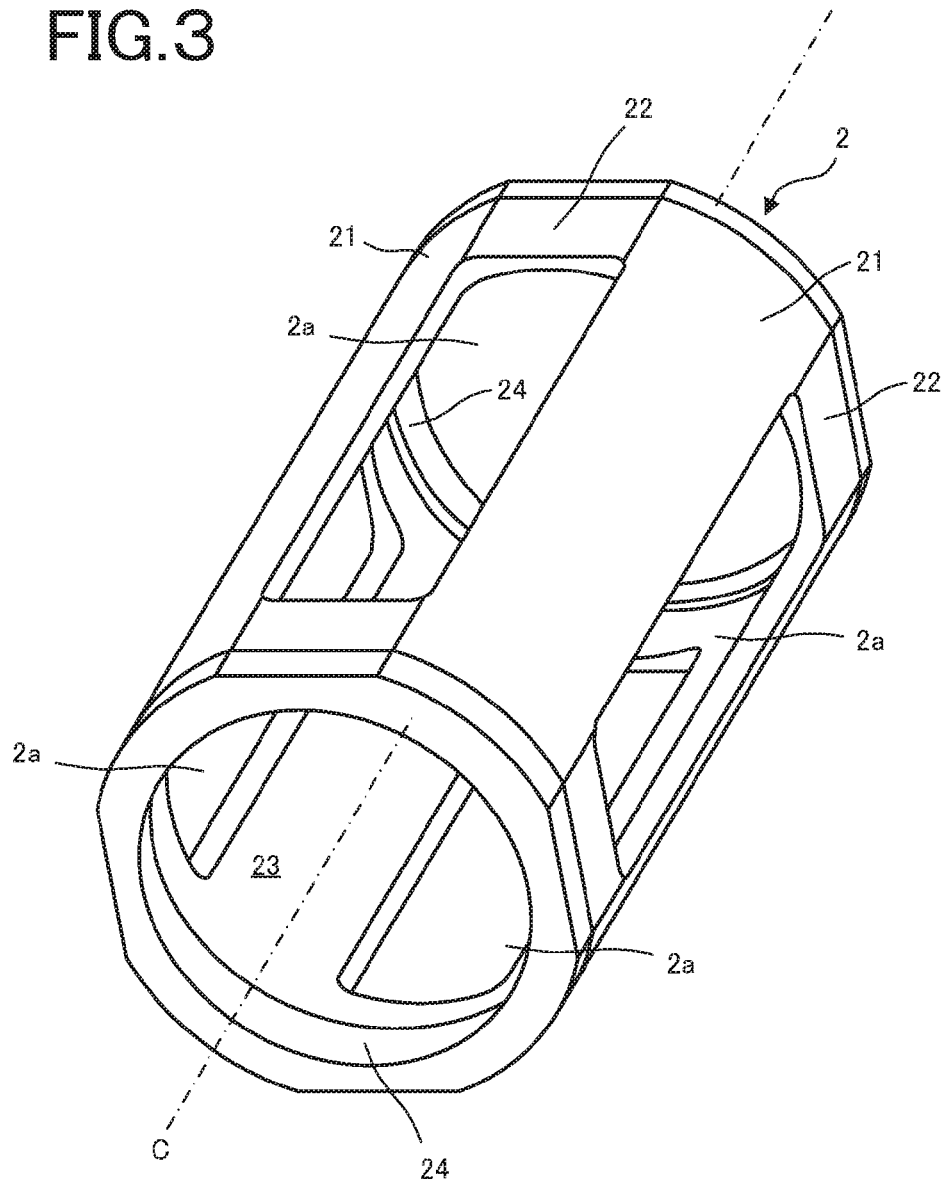
FIG. 3 is illustrative of the fixed part in the optical unit according to the first embodiment.
Figure 4:
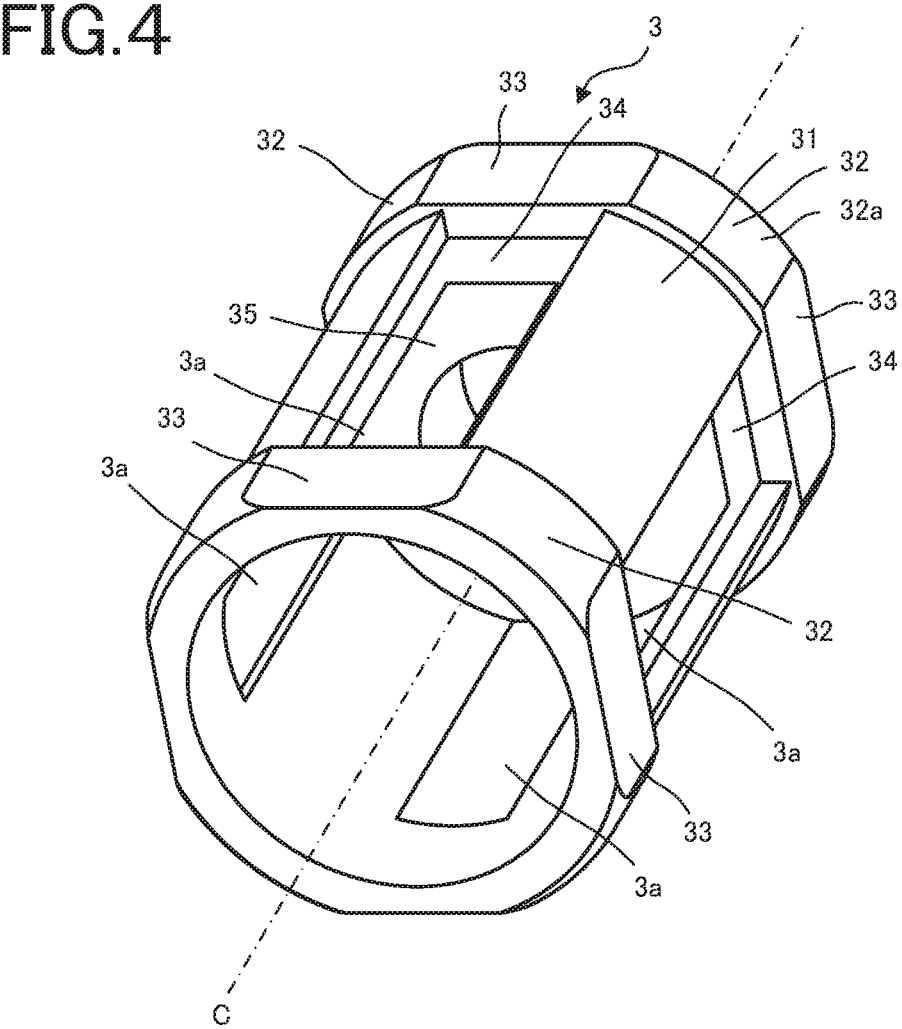
FIG. 4 is illustrative of the movable part in the optical unit according to the first embodiment.

FIG. 1 is a sectional view of the optical unit according to the first embodiment of the invention as taken orthogonally with respect to its axis, and FIG. 2 is a sectional view of the optical unit according to the first embodiment including its axis. It is here to be noted that FIG. 1 is a sectional view of FIG. 2 as taken on section I-I and FIG. 2 is a sectional view of FIG. 1 as taken on section II-II. FIG. 3 is illustrative of the fixed part in the optical unit according to the first embodiment, and FIG. 4 is illustrative of the movable part in the optical unit according to the first embodiment.

The optical unit 1 according to the embodiment described herein includes a fixed part 2, a movable part 3 that is movable relative to the fixed part 2, a front frame part 4 attached to the object side of the fixed part 2, a back frame part 5 attached to the image side of the fixed part, and a voice coil motor 10 that generates a driving force for movement of the movable part 3 relative to the fixed part 2.

The fixed part 2 includes a member having a tubular form with respect to a given axis C. The fixed part 2 according to the embodiment described herein includes a tubular member 21 and a planar portion 22 formed on a part of the outer circumference side of the tubular member 21. Note here that the inner circumference side of the planar portion 22 may be in a cylindrical shape. A part of the planar portion 22 is lightened as indicated by 2a. In the first embodiment described herein, there are four diametrically orthogonal planar portions 22 provided for each 90° with the axis C of the tubular member 21 as center. Each planar portion 22 includes a lightened site in the form of an opening 2a in a position except both its axial ends. Note here that the opening 2a may be formed in at least a part of the planar portion 22 or, alternatively, it may protrude out of a part of the tubular member 21. At both ends of the fixed part 2 according to the first embodiment, there are inwardly protruding thicker portions 24 formed. Note here that the thicker portion 24 may be formed separately from the tubular member 21 and planar portion 22, and made integral with them at the time of later assembling.

The movable part 3 includes a member having a tubular form with respect to a given axis C. The movable part 3 according to the embodiment described herein includes a tubular member 31, protruding edges 32 formed at both ends of the tubular member 31 in the axis C direction of the tubular member 31 and having an outer diameter larger than the diameter of the tubular member 31, a planar portion 33 formed on a part of the outer circumference side of the protruding edge 32, a step 34 formed between the planar portions 33 at both the ends in the axis C direction and nearer to the inner circumference side of the tubular member 31, and a small inner-diameter portion 35 formed on one side of the axis C direction and having an inner diameter smaller than the diameter of the inner circumference surface of the tubular member 31. The tubular member 31 and protruding edge 32 of the movable part 3 may be assembled of separate members.

A part of the step 34 is provided with an opening 3a, and a recess 3b is formed in an outer end surface of the small-diameter portion 35 in the axis C direction. In the first embodiment, there are four steps 34 provided for each 90° with the axis C of the tubular member 31 as center, and a part of each step 34 is provided with an opening 3a. The respective steps 34 form four diametrically orthogonal planes for each 90° with respect to the center of the axis C.

The front frame part 4 is a tubular member including an outer circumference portion 41 and an inner circumference portion 42. The outer circumference portion 41 includes a first outer circumference component 41a, a second outer circumference component 41b, a third outer circumference component 41c, a first outer step component 41d and a second outer step component 41e. The inner circumference portion 42 includes a first inner circumference component 42a, a second inner circumference component 42b, a third inner circumference component 42c, a first inner step component 42d and a second inner step component 42e.

The first outer circumference component 41a is the diametrically largest of the outer circumference portion 41, and the third outer circumference component 41c is the diametrically smallest of the outer circumference portion 41. The second outer circumference component 41b has a length halfway between the lengths of the first outer circumference component 41a and the third outer circumference component 41c. There is the first outer step component 41d formed between the first outer circumference component 41a and the second outer circumference component 41b, and there is the second outer step component 41e formed between the second outer circumference component 41b and the third outer circumference component 41c.

The first inner circumference component 42a is the diametrically largest of the inner circumference portion 42, and the third inner circumference component 42c is the diametrically smallest of the inner circumference portion 42. The second inner circumference component 42b has a length halfway between the lengths of the first inner circumference component 42a and the third inner circumference component 42c. There is the first inner step component 42d formed between the first inner circumference component 42a and the second inner circumference component 42b, and there is the second inner step component 42e formed between the second inner circumference component 42b and the third inner circumference component 42c.

The front frame part 4 is inserted such that the third outer circumference component 41c is located inside the inner circumference surface of the movable part 3, and the second outer circumference component 41b is inserted while coming in contact with the inner circumference surface 23 of the fixed part 2 until the object-side end of the fixed part 2 is in contact with the first outer step component 41d. Note here that the object-side end of the fixed part 2 may be in no contact with the first outer step component 41d.

There is a moving lens group Gv held at the small-diameter portion 35 of the movable part 3. In the first embodiment of the invention, for instance, the moving first lens Lv1 and moving second lens Lv2 are held at the small-diameter portion 35.

A front lens group Gf is held at the front frame part 4. In the first embodiment of the invention, for instance, the front frame part 4 holds a front first lens Lf1 on the first inner circumference component 42a, a front second lens Lf2 on the second inner circumference component 42b, and a front third lens Lf3 on the third inner circumference component 42c.

There is a back lens group Gb held at the back frame part 5. In the first embodiment of the invention, for instance, the back frame part 5 holds a back first lens Lb1 on the inner circumference surface.

The voice coil motor 10 includes a coil 11 located in the fixed part 2 and a magnet 12 located in the movable part 3 in such a way as to be opposite to the coil 11.

As shown in FIG. 2, the coil 11 in the first embodiment of the invention includes a first coil 11a wound around the outer circumference of the fixed part 2, and a second coil 11b that is wound around the outer circumference of the fixed part 2 while standing side by side in the axis C direction of the first coil 11a. It is preferable that the first coil 11a and the second coil 11b adjacent to each other in the axis C direction have lead wires wound in opposite directions and connected in series. The first coil 11a has a plane 11ap corresponding to the opening 2a in the fixed part 2. That is, the first coil 11a has an arrangement wherein the planar portion 11ap and the cylindrical portion 11 at are alternately located in the circumferential direction. Note here that the second coil 11b has the same arrangement too.

Referring here to the magnet 12, a first magnet 12a and a second magnet 12b in opposition to the planar portions 11p of the first coil 11a and the second coil 11b are located on the step 34 of the movable part 3 in the axis C direction for each 90° with respect to the axis C center, as shown in FIG. 2. This makes sure stable placement of the first magnet 12a and second magnet 12b, resulting in prevention of shakes of the movable part 3 upon moving relative to the fixed part 2 due to the creation of a stable magnetic field.

Preferably, the total of the widths of the first coil 11a and second coil 11b in the axis C direction is greater than the width of the first magnet 12a and the second magnet 12b in the axis C direction such that within the moving range of the movable part 3, the first magnet 12a and second magnet 12b lie always in the widths of the first coil 11a and second coil 11b in the axis C direction.

With the magnet 12 placed in the movable part 3, the diametrically outer surface of the magnet 12 is located in the opening 2a in the fixed part 2, as shown in FIGS. 1 and 2. In other words, a first distance from the axis C to the diametrically outer surface of the magnet 12 is longer than a second distance from the axis C to the inner circumference surface 23 of the fixed part 2.

Referring here to the optical unit 1 according to the first embodiment of the invention, at least a part of the movable part 3 is included in a portion of the front frame part 4 projected in the axis C direction, as shown in FIG. 1. To put it another way, a distance L31 to the inner circumference surface 31a of the tubular member 31 of the movable part 3 is shorter than a distance L41 from the axis C to the first outer circumference component 41a of the front frame part 4 having the largest diameter, and longer than a distance L42 from the axis C to the third inner circumference component 42c of the front frame part 4 having the smallest diameter.

The size and weight of the optical unit 1 can thus be reduced with the result that the driving efficiency of the optical unit 1 is boosted up enough for rapid movement of the movable part 3.

Referring again to the optical unit 1 according to the first embodiment, it is more preferable that at least a part of the movable part 3 is included in a portion of the back frame part 5 projected in the axis C direction, as shown in FIG. 2. In another parlance, a distance L31 to the inner circumference surface 31a of the tubular member 31 of the movable part 3 is shorter than a distance L51 from the axis C to the outer circumference component 51a of the back frame part 5 having the largest diameter, and longer than a distance L52 from the axis C to the inner circumference component 52a of the back frame part 5 having the smallest diameter. This makes it possible to reduce the size and weight of the optical unit 1 in its diametrical direction.

Referring further to the optical unit 1 according to the first embodiment, it is more preferable that at least a part of the front frame part 4 is inserted into the movable part 3, as shown in FIG. 2. For instance, it is preferable that the third outer circumference component 41c of the front frame part 4 having the smallest diameter is inserted inside the inner circumference surface 31a of the tubular member 31 of the movable part 3 because the size and weight of the optical unit 1 can be reduced in the axis C direction.

It is here to be noted that at least a part of the back frame part 5 may also be inserted inside the inner circumference surface 31a of the tubular member 31 of the movable part 3 because the size and weight of the optical unit 1 may be reduced in the axis C direction.

As shown in FIG. 1, the outer circumference surface of the protruding edge 32 of the movable part 3 forms a sliding surface 32a in contact with the inner circumference surface 23 of the fixed part 2. Contact of the inner circumference surface 23 of the fixed part 2 with the sliding surface 32a of the movable part 3 allows for movement of the movable part 3 while it comes constantly in contact with the fixed part 2. In turn, this prevents tilting of the movable part 3 relative to the fixed part 2, making sure unerring movement of the movable part 3.

Further, it is preferable that the optical unit 1 is formed symmetrically with respect to the axis C. The structure allowing for contact of the inner circumference surface 23 of the fixed part 2 with the sliding surface 32a of the movable part 3 is combined with the symmetrical configuration of the whole optical unit 1 with respect to the axis C so that the center of gravity can be positioned on the axis C, contributing to further prevention of tilting of the movable part 3 relative to the fixed part 2.

While the magnets 12 are placed for each 90° with the axis C as center in the first embodiment, it is to be understood that they may be placed at any desired angles other than 90°.

Figure 5:
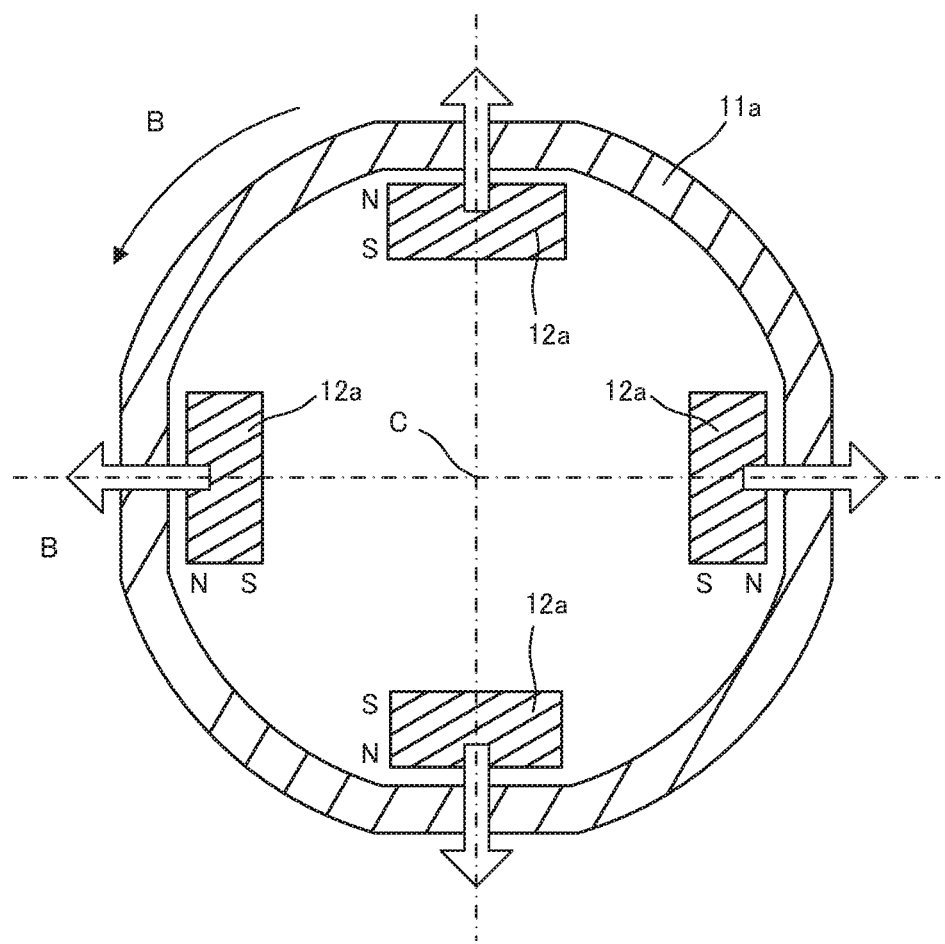
FIG. 5 is a sectional view of the direction of polarization of the magnet in the optical unit according to the first embodiment as taken orthogonally with respect to the axis.
Figure 6:
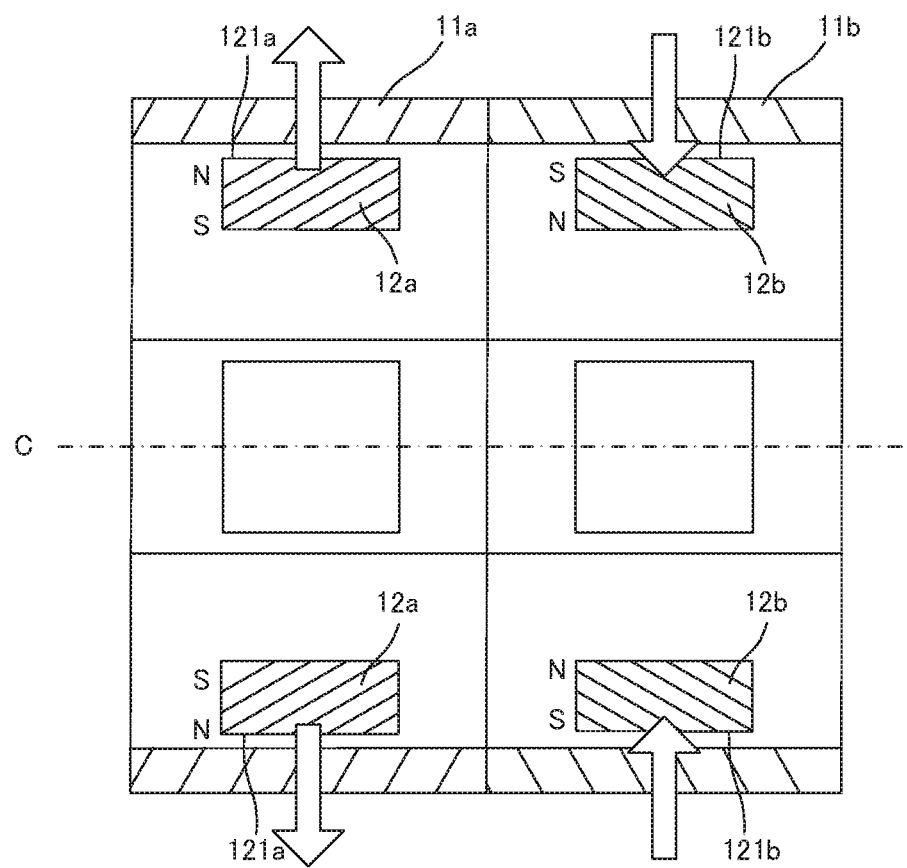
FIG. 6 is a sectional view of the direction of polarization of the magnet in the optical unit according to the first embodiment including the axis.

FIG. 5 is a sectional view indicative of the direction of polarization of the magnet in the optical unit according to the first embodiment of the invention as taken orthogonally with respect to the axis, and FIG. 6 is an axially sectional view indicative of the direction of polarization of the magnet in the optical unit according to the first embodiment.

Referring now to the magnet 12 according to the embodiment described herein, a set of the first magnets 12a and a set of the second magnets 12b are located side by side and spaced away from one another in the axis C direction. Preferably, the set of the first magnets 12a and the set of the second magnets 12b are diametrically magnetized with the magnetic poles in opposite directions. For instance, the first magnet 12a may be magnetized as an N-pole on the first coil 11a side whereas the opposite side may be done as an S-pole, and the second magnet 12b may be magnetized as an S-pole on the second coil 11b side whereas the opposite side may be done as an N-pole. As indicated by hollow arrows in FIGS. 5 and 6, it is preferable that the directions of polarization of the magnets 12 are determined in the directions orthogonal to the axis C. It is also preferable that the winding direction of the coil 11 is reversed between the set of the first magnets 12a and the set of the second magnets 12b. As shown typically in FIG. 5, when the first coil 11a is wound in a direction indicated by an arrow B, the second coil 11b may be wound in the opposite direction.

In the first embodiment of the invention, the movable part 3 having the first magnets 12a positioned in opposition to the first coils 11a is located on the inner circumference side of the fixed part 2 having the first coils 11a wound around, as shown in FIG. 1. Accordingly, the planar portion 11ap of the first coil 11a lies in a magnetic field in the direction orthogonal to the diametrically outer surface 121a of the first magnet 12a. Note here that the second magnet 12b is also similarly constructed. Thus, the driving efficiency is boosted up enough for rapid movement of the movable part 3, and the first magnet 12a and second magnet 12b are easy to assemble because the diametrically outer surfaces 121a and 121b are each formed of a plane.

Upon the passage of electric current through the coil 11 in the optical unit 1 having such structure, an axis C direction force is generated in the movable part 3 under the influence of the magnetic field of the magnet 12 with the result that the movable part 3 moves in the axis C direction relative to the fixed part 2, as indicated by an action arrow A in FIG. 2. For instance, electric currents through the first coil 11a and second coil 11b may be controlled such that the movable part 3 moves relative to the fixed part 2. Note here that even while the movable part 3 is moving, the diametrically outer surface of the magnet 12 remains located within the opening 2a in the fixed part 2.

Thus, the size and weight of the optical unit 1 according to the embodiment described herein can be reduced, so the driving efficiency can be boosted up for rapid movement of the movable part 3. During operation too, the inner circumference surface 23 of the fixed part 2 remains into contact with the sliding surface 32a of the movable part 3 so that any tilting of the movable part 3 relative to the fixed part 2 can be held back for unerring movement of the movable part 3.

Figure 7:
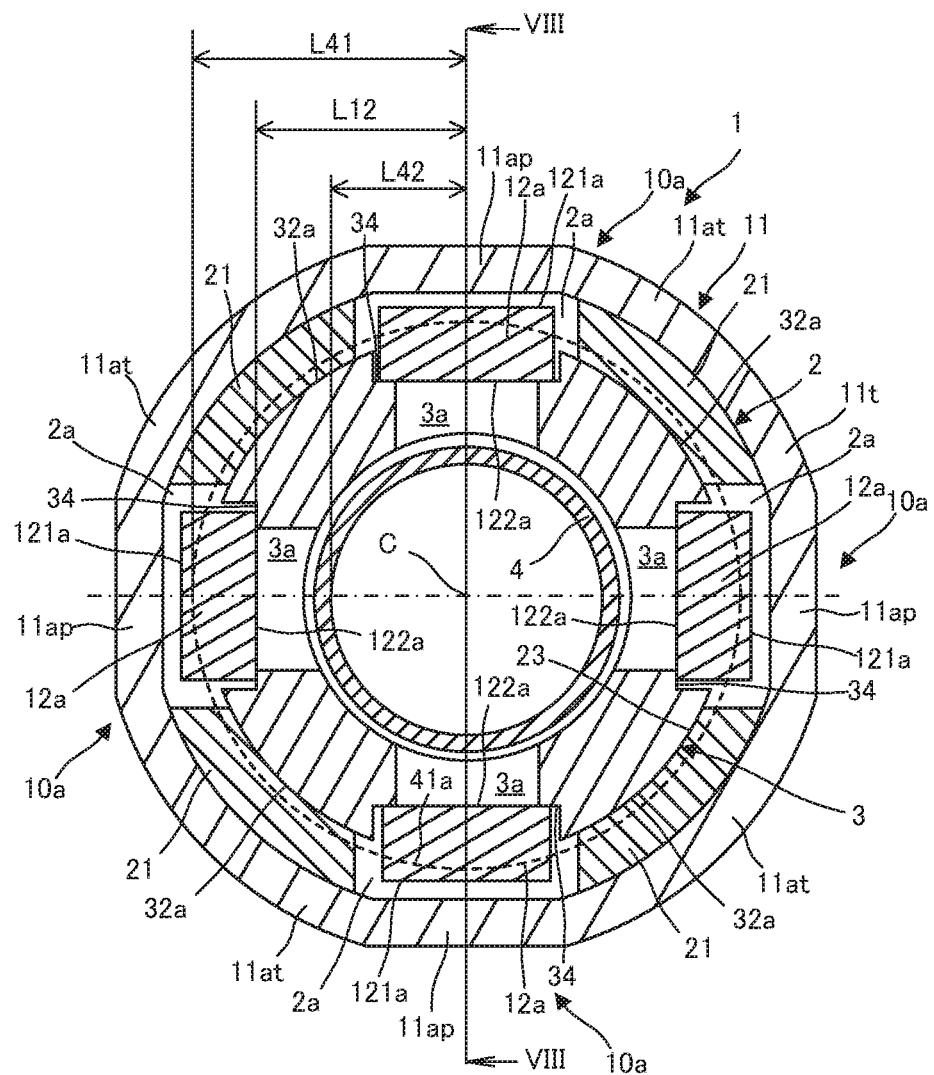
FIG. 7 is a sectional view of the optical unit according to the second embodiment of the invention as taken orthogonally with respect to its axis.
Figure 8:
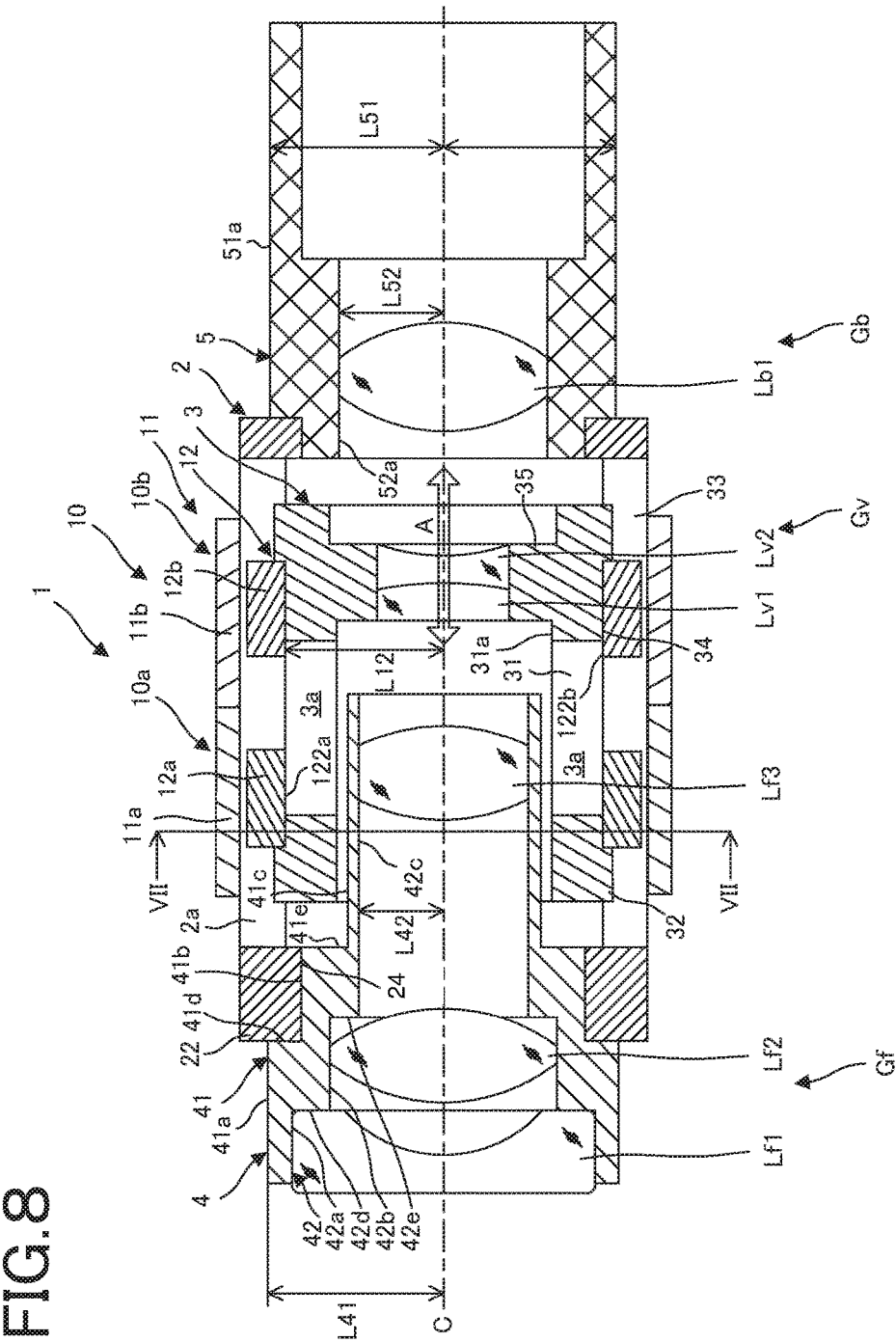
FIG. 8 is a sectional view of the optical unit according to the second embodiment including its axis.

FIG. 7 is a sectional view of the optical unit according to the second embodiment of the invention as taken orthogonally with respect to the axis, and FIG. 8 is a sectional view of the optical unit according to the 10 second embodiment including the axis. Note here that FIG. 7 is a sectional view of FIG. 8 as taken on section VII-VII and FIG. 8 is a sectional view of FIG. 7 as taken on section VIII-VIII.

The optical unit 1 according to the second embodiment is substantially the same in construction as the optical unit 1 according to the first embodiment with the exception of the following points.

In the optical unit 1 according to the second embodiment here, at least a part of the magnet 12 is included in a portion of the front frame part 4 projected in the axis C direction, as can be seen from FIG. 7. To put it another way, a distance L12 from the axis C to the innermost surface 122a, 122b of the magnet 12 is shorter than a distance L41 from the axis C to the first outer circumference component 41a of the front frame part 4 having the largest diameter, and longer than a distance L42 from the axis C to the third inner circumference component 42c of the front frame part 4 having the smallest diameter.

Thus, the size and weight of the optical unit 1 can be reduced, so the driving efficiency can be boosted up for rapid movement of the movable part 3.

It is here to be appreciated that in the optical unit 1 according to the second embodiment, at least a part of the magnet 12 is included in a portion of the back frame part 5 in the axis C direction, as shown in FIG. 8. In another parlance, the distance L12 from the axis C to the innermost surface 122a, 122b of the magnet 12 is preferably shorter than a distance L51 from the axis C to the outer circumference component 51a of the back frame part 5 having the largest diameter, and longer than a distance L52 from the axis C to the inner circumference component 52a of the back frame part 5 having the smallest diameter. Thus, the size and weight of the optical unit 1 can be reduced in the diametrical direction.

Figure 9:
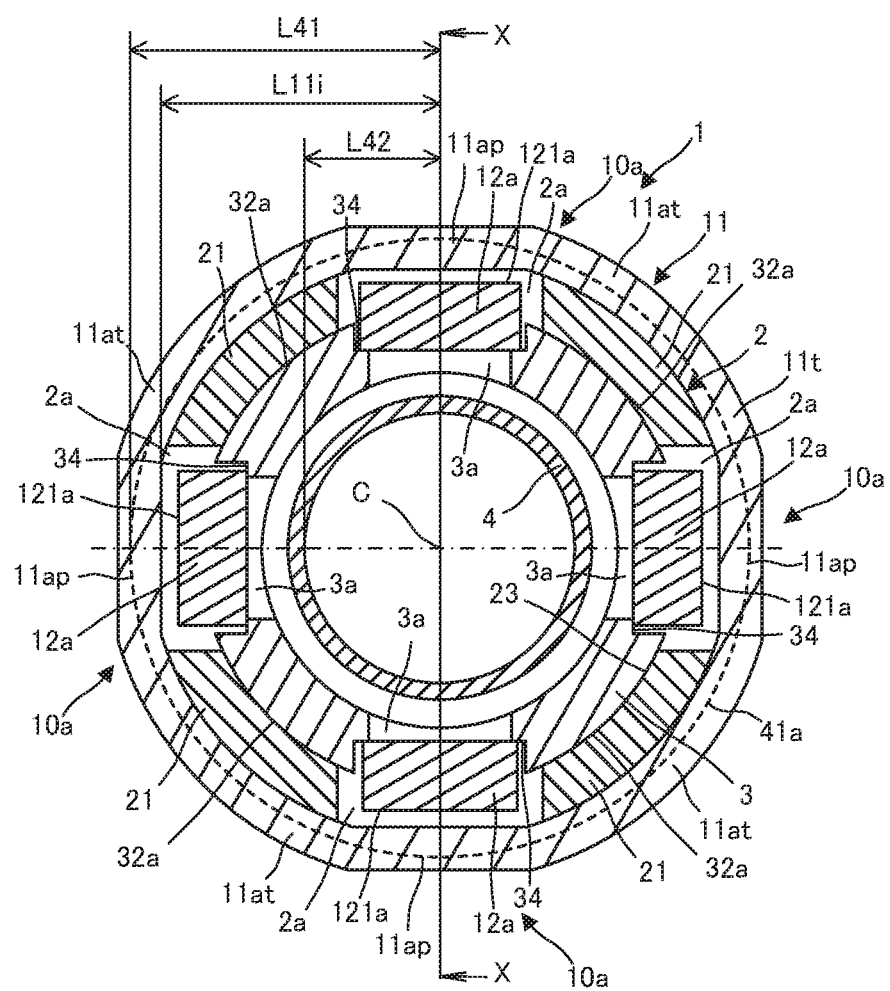
FIG. 9 is a sectional view of the optical unit according to the third embodiment of the invention as taken orthogonally with respect to its axis.
Figure 10:
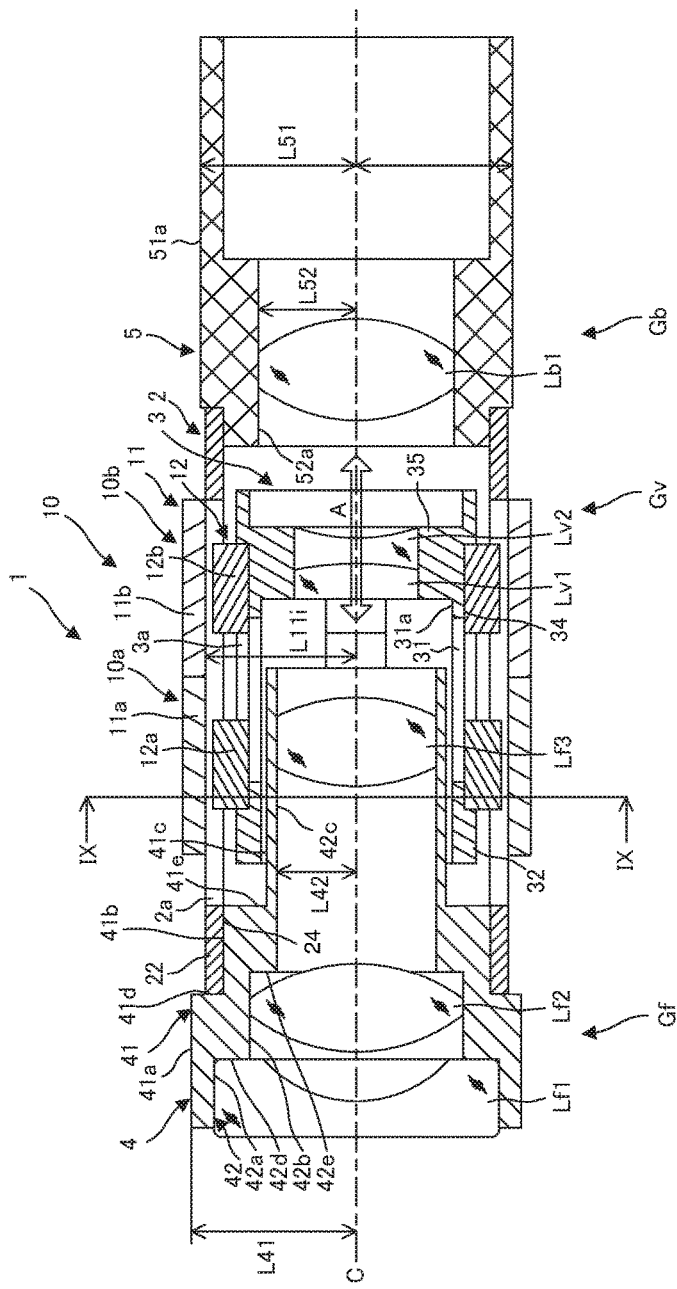
FIG. 10 is a sectional view of the optical unit according to the third embodiment including its axis.
Figure 11:
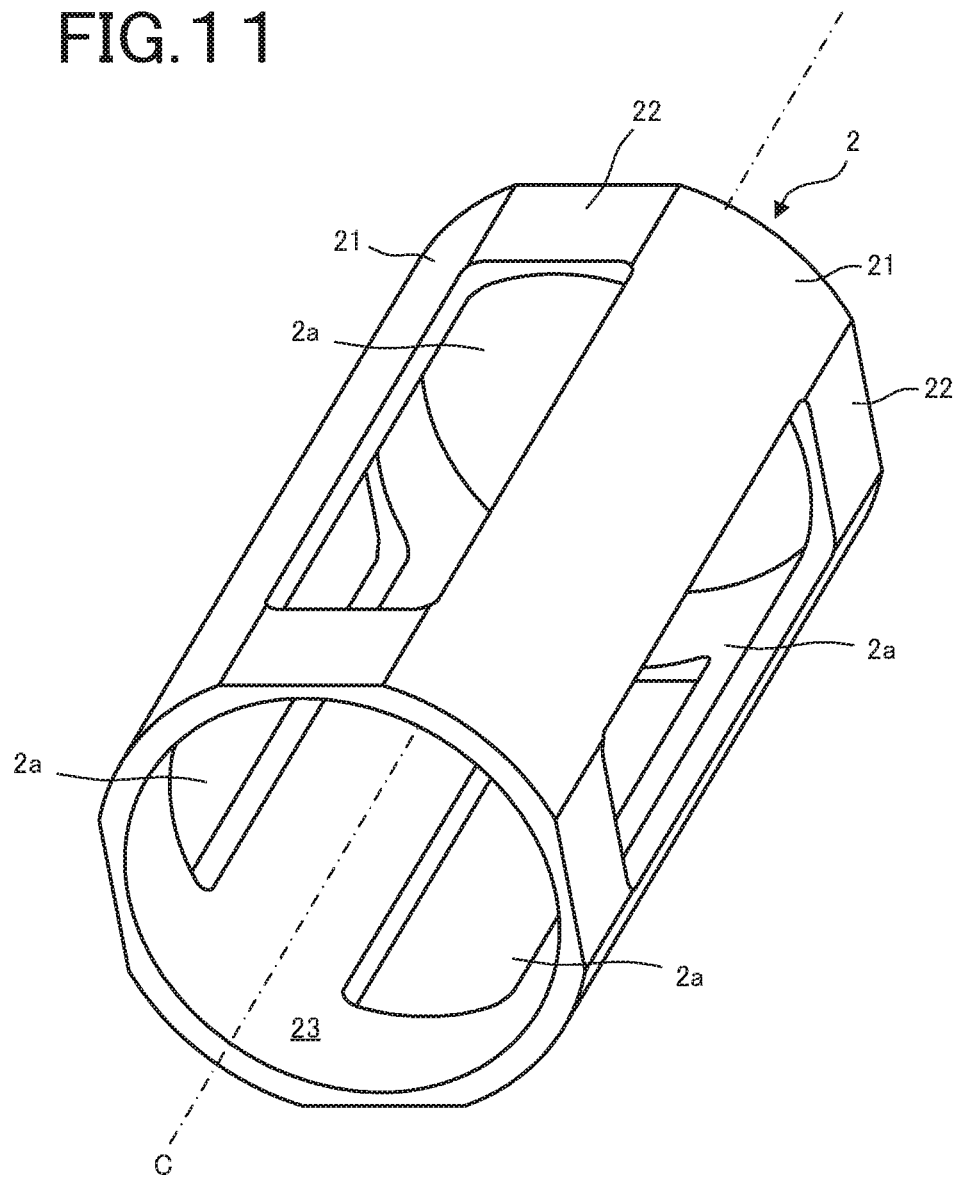
FIG. 11 is illustrative of the fixed part in the optical unit according to the third embodiment.

FIG. 9 is a sectional view of the optical unit according to the third embodiment of the invention as taken orthogonally with respect to the axis, and FIG. 10 is a sectional view of the optical unit according to the third embodiment including the axis. Note here that FIG. 9 is a sectional view of FIG. 10 as taken on section IX-IX and FIG. 10 is a sectional view of FIG. 9 as taken on section X-X. FIG. 11 is illustrative of the fixed part in the optical unit according to the third embodiment.

The optical unit 1 according to the third embodiment is substantially the same in construction as the optical unit 1 according to the first and second embodiments with the exception of the following points.

In the optical unit 1 according to the third embodiment here, at least a part of the coil 11 is included in a portion of the front frame part 4 projected in the axis C direction. To put it another way, a distance L11i from the axis C to the innermost surface of the coil 11 is shorter than the distance L41 from the axis C to the first outer circumference component 41a of the front frame part 4 having the largest diameter, and longer than the distance L42 from the axis C to the third inner circumference component 42c of the front frame part 4 having the smallest diameter. Note here that the fixed part 2 according to the third embodiment is not provided with any thicker portion.

Thus, the size and weight of the optical unit 1 can be reduced with the result that the driving efficiency of the optical unit 1 can be boosted up for rapid movement of the movable part 3.

It is more preferable that in the optical unit 1 according to the third embodiment, at least a part of the coil 11 is included in a portion of the back frame part 5 projected in the axis C direction, as shown in FIG. 10. In another parlance, the distance L11i from the axis C to the innermost surface of the coil 11 is preferably shorter than the distance L51 from the axis C to the outer circumference component 51a of the back frame part 5 having the largest diameter, and longer than the distance L52 from the axis C to the inner circumference component 52a of the back frame part 5 having the smallest diameter. Thus, the size and weight of the optical unit 1 can be reduced in the diametrical direction.

Figure 12:
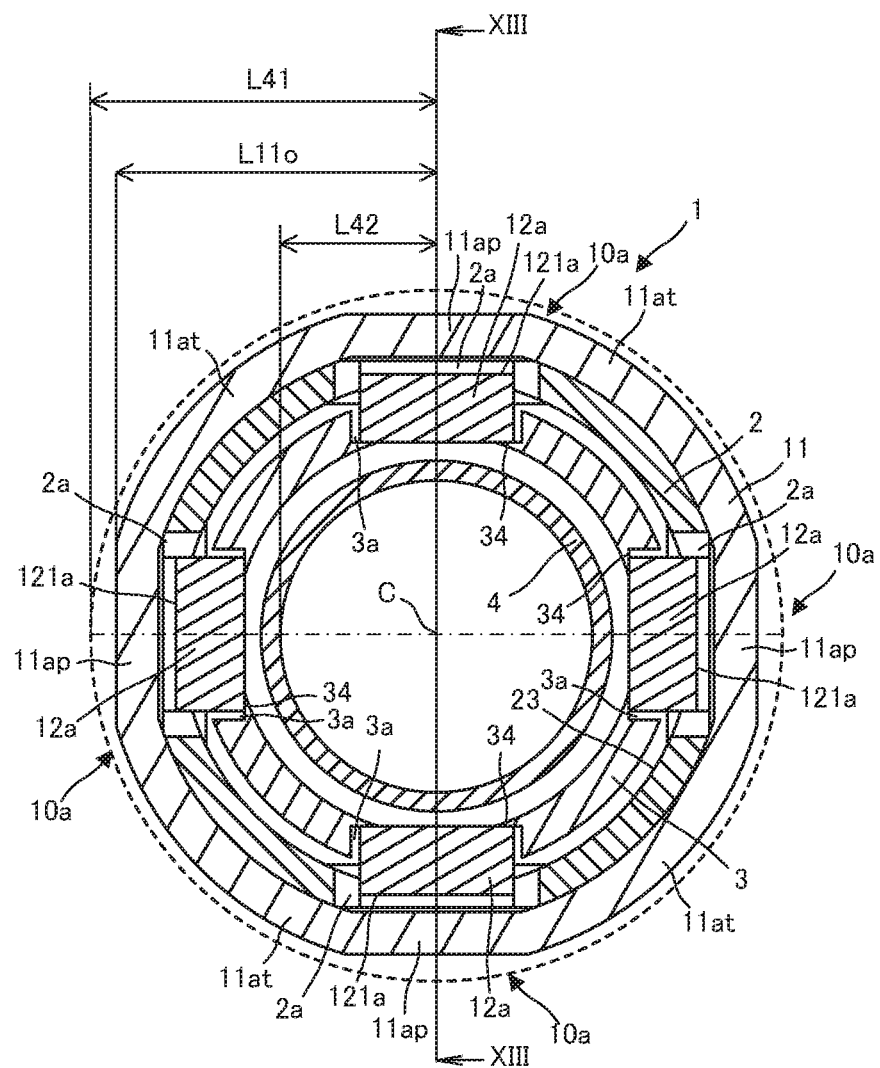
FIG. 12 is a sectional view of the optical unit according to the fourth embodiment of the invention as taken orthogonally with respect to its axis.
Figure 13:
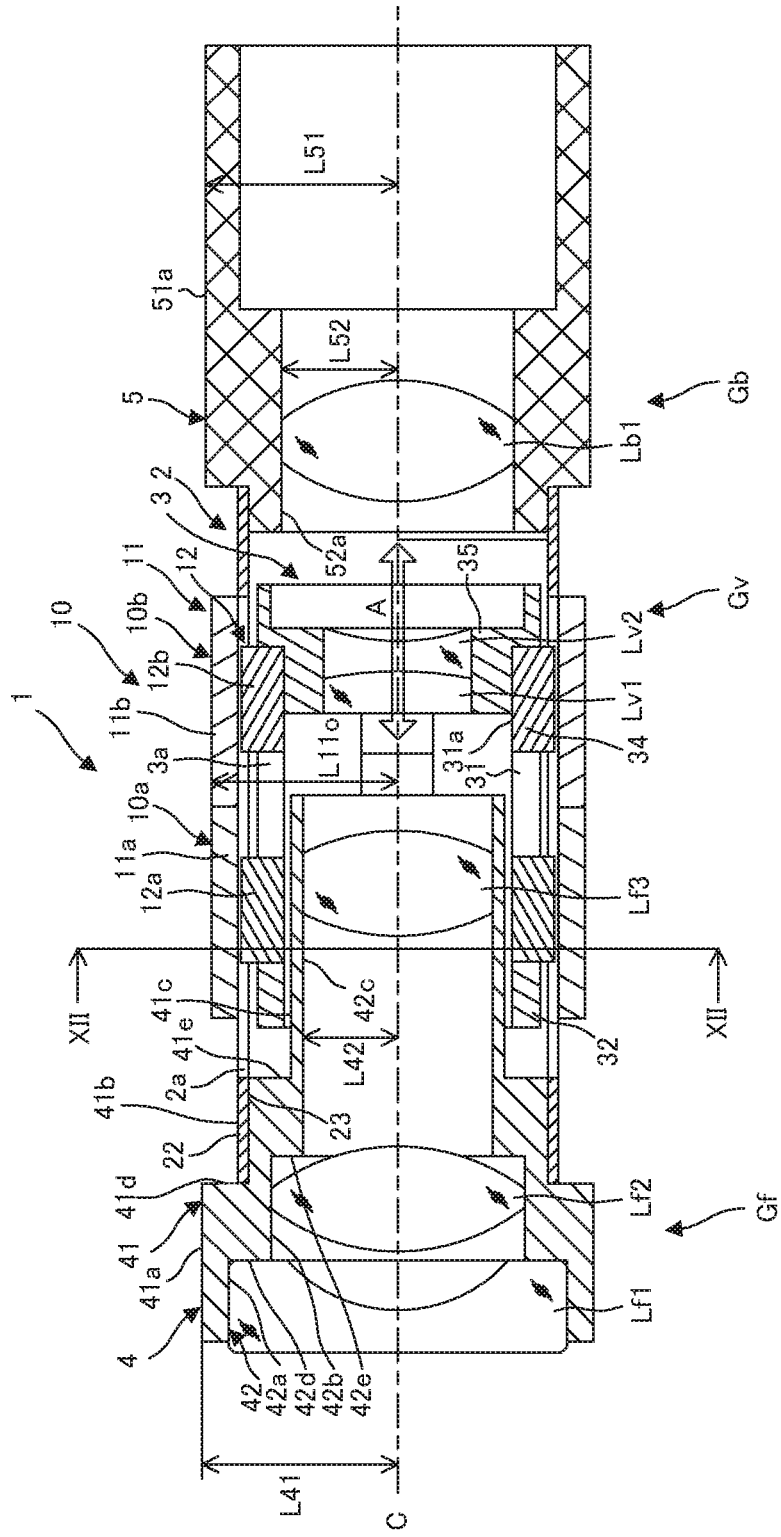
FIG. 13 is a sectional view of the optical unit according to the fourth embodiment including its axis.

FIG. 12 is a sectional view of the optical unit according to the fourth embodiment of the invention as taken orthogonally with respect to the axis, and FIG. 13 is a sectional view of the optical unit according to the fourth embodiment including the axis. Note here that FIG. 12 is a sectional view of FIG. 13 as taken on section XII-XII and FIG. 13 is a sectional view of FIG. 12 as taken on section XIII-XIII.

The optical unit 1 according to the fourth embodiment is substantially the same in construction as the optical unit 1 according to the first, second and third embodiments with the exception of the following points.

In the optical unit 1 according to the fourth embodiment of the invention, the coil 11, magnet 12, fixed part 2 and movable part 3 are all included in a portion of the front frame part 4 projected in the axis C direction, as shown in FIGS. 12 and 13. To put it another way, a distance L11o from the axis C to the outermost circumference surface of the coil 11 is shorter than the distance L41 from the axis C to the first outer circumference component 41a of the front frame part 4 having the largest diameter, and longer than the distance L42 from the axis C to the third inner circumference component 42c of the front frame part 4 having the smallest diameter.

Thus, the size and weight of the optical unit 1 can be reduced with the result that the driving efficiency of the optical unit 1 can be boosted up for rapid movement of the movable part 3.

It is more preferable that in the optical unit 1 according to the fourth embodiment, the coil 11, magnet 12, fixed part 2 and movable part are all included in a portion of the back frame part 5 projected in the axis C direction, as shown in FIG. 13. In another parlance, the distance L11o from the axis C to the outermost surface of the coil 11 is preferably shorter than the distance L51 from the axis C to the outer circumference component 51a of the back frame part 5 having the largest diameter, and longer than the distance L52 from the axis C to the inner circumference component 52a of the back frame part 5 having the smallest diameter. Thus, the size and weight of the optical unit 1 can be reduced in the diametrical direction.

Figure 14:
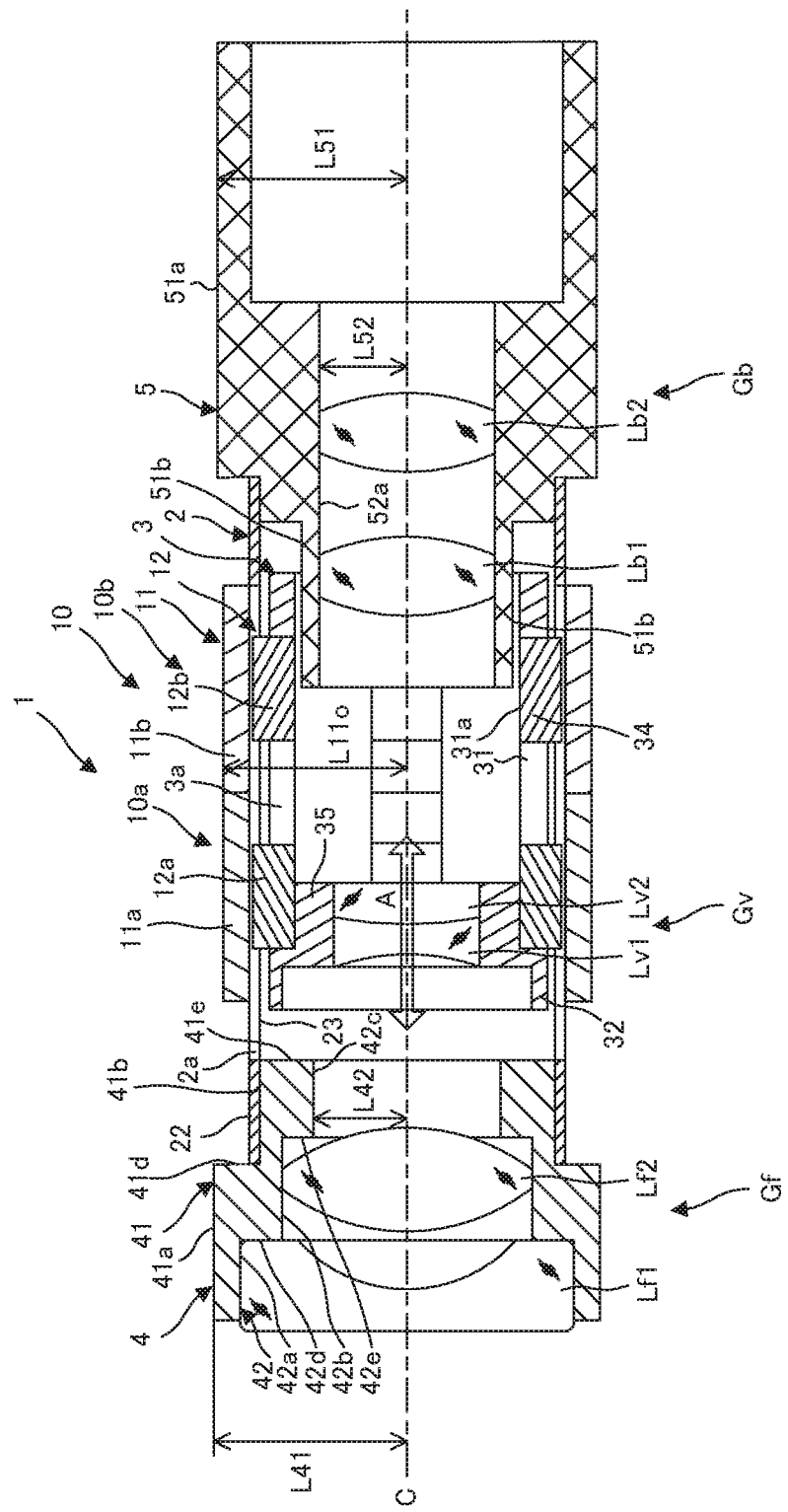
FIG. 14 is a sectional view of the optical unit according to the fifth embodiment of the invention including its axis.

FIG. 14 is a sectional view of the optical unit according to the fifth embodiment of the invention including the axis.

The optical unit according to the fifth embodiment is an example wherein the coil 11, magnet 12, fixed part 2 and movable part 3 are all included in a portion of the back frame part 5 projected in the axis C direction. In other words, the distance L11o from the axis C to the outermost circumference surface of the coil 11 is shorter than the distance L51 from the axis C to the outer circumference component 51a of the back frame part 5 having the largest diameter, and longer than the distance L52 from the axis C to the inner circumference component 52a of the back frame part 5 having the smallest diameter. Thus, the size and weight of the optical unit 1 can be reduced in the diametrical direction.

In the optical unit 1 according to the fifth embodiment of the invention, at least a part of the back frame part 5 is inserted into the movable part 3, as shown in FIG. 14. For instance, it is preferable that the outer circumference component 51b of the back frame part 5 having the smallest diameter is inserted inside the inner circumference surface 31a of the tubular member 31 of the movable part 3. Thus, the size and weight of the optical unit 1 can be reduced in the axis C direction.

The optical unit 1 according to the embodiment described herein includes various types of image sensors such as CCDs or CMOSs, and may include in the back frame part 5 an imaging device IS (not shown) having a light-receiving portion on the image plane. Adjacent to the object side of the imaging device IS there may be a filter or cover glass or other optical element OD (not shown) located. Note here that the lens arrangements of the front lens group Lf, back lens group Lb and moving lens group Gv are not limited to the embodiment described herein, so they may be modified as required.

Referring to the optical unit 1 according to the embodiment described herein, it is when the movable part 3 is positioned on the most image side of the movable range that the taking magnification gets highest, and it is when the movable part 3 is positioned on the most object side of the movable range that the taking magnification gets lowest. In other words, it is when the movable part 3 is positioned on the most image side of the movable range that the focal length gets longest and there is a telephoto-end state available with a narrow field of view, and it is when the movable part 3 is positioned on the most object side of the movable range that the focal length becomes shortest and there is a wide-angle state available with a wide field of view.

In this conjunction, the optical unit 1 according to such embodiments as described above may be used with an electronic camera apparatus in general and an endoscope in particular, as embodied just below.

Figure 15:
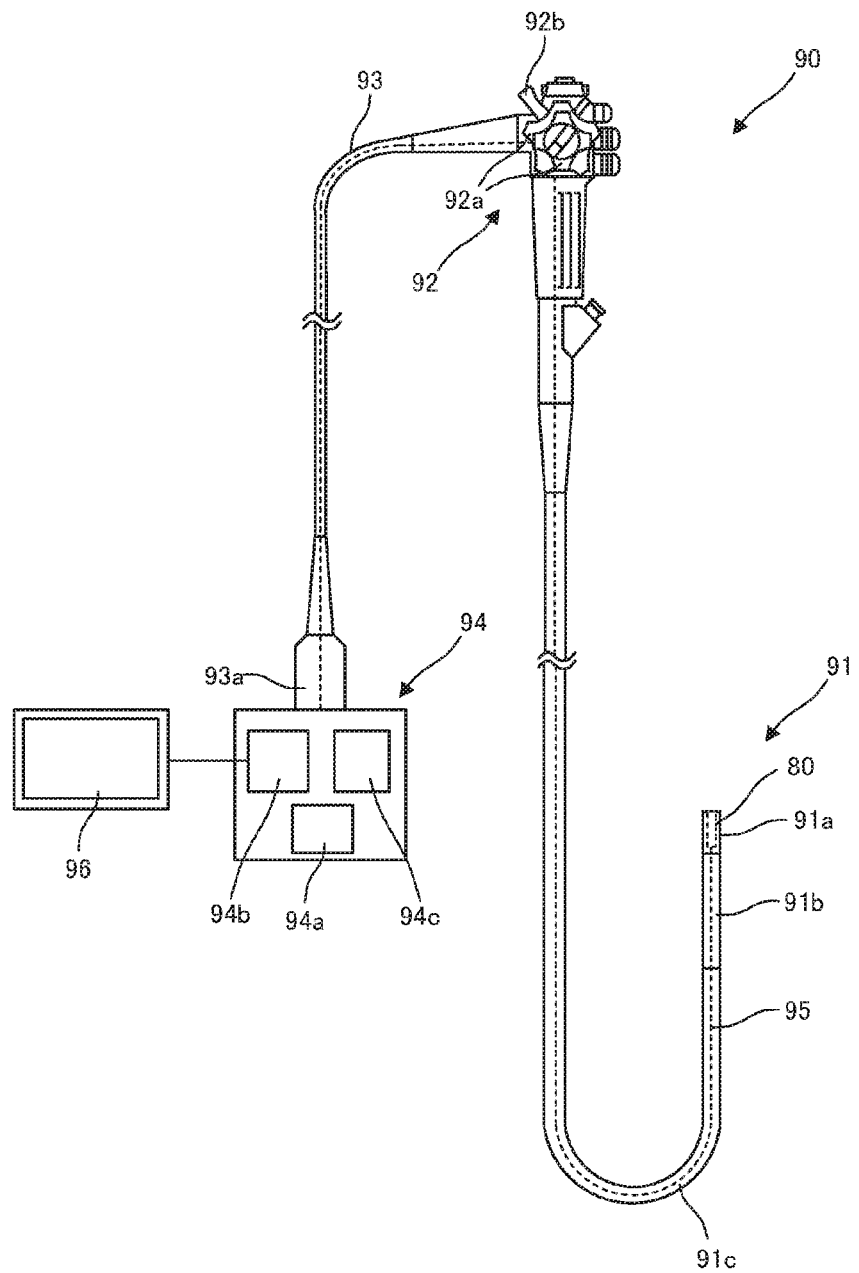
FIG. 15 is illustrative of one example of the endoscope including the optical unit according to one embodiment of the invention.

FIG. 15 is illustrative of one example of the endoscope including the optical unit according to the embodiment described herein.

The endoscope 90 according to the embodiment described herein is capable of insertion through a subject of interest such as the human body for optical taking of a given site of interest in the subject. Note here that the subject through which the endoscope 90 is to be inserted may be living bodies inclusive of the human body as well as artifacts such as machinery and buildings.

The endoscope 90 includes an insert part 91 inserted through the interior of the subject of interest, an operating unit 92 positioned at the proximal end of the insert part 91 and a universal cable 93 that is a composite cable extended out from the operating unit 92.

The insert part 91 includes a distal-end portion 91a attached to the distal end, a curving portion 91b located on the proximal end side of the distal-end portion 91a and a flexible tubular portion 91c located on the proximal end side of the curving portion 91b and connected to the distal end side of the operating unit 92. The distal-end portion 91a has the optical unit 1 built inside. Note here that the endoscope 90 used may be a hard one having no flexible tubular portion 91c in the insert part 91.

The operating unit 92 includes an angle operating portion 92a for operation of the curving state of the curving portion 91b and a zoom operating portion 92b for giving an instruction to the voice coil motor 10 to implement zoom operation of the optical unit 1. The angle operating portion 92a has a knob form and the zoom operating portion 92b has a lever form; however, they may each be configured as a volume switch, a push switch or the like.

The universal cord 93 is a member for connecting the operating unit 92 to external hardware 94 by way of a connector 93a. The external hardware 94 includes a driving control portion 94a for controlling the curving state of the curving portion 91b, an image control portion 94b for controlling the imaging apparatus 80, a light source (not shown) and a light source control portion 94c for controlling the light source, and the like.

A cable 95 such as a wire, an electric wire, an optical fiber or the like is inserted through the insert part 91, operating unit 92 and universal cord 93. The wire is provided so as to connect the driving control portion 94a located in the external hardware 94 to the operating unit 92 and curving portion 91b, the electric wire is provided for electric connections between the optical unit 1 and the operating unit 92 and image control portion 94b, and the optical fiber is provided for optical connections between the light source and the operating unit 92 and light source control portion 94c.

The driving control portion 94a is built up of an actuator or the like to move the wire advanceably and retractably for control of the curving state of the curving portion 91b. The image control portion 94b implements driving control of the voice coil motor 10 built in the optical unit 1 and processing of images taken through the imaging device IS. The images processed by the image control portion 94b appear on an image display 96. The light source control portion 94c is provided so as to control the brightness of light exiting out from the distal-end portion 91a, and so on.

It is here to be appreciated that the operating unit 92 and external hardware 94 may be formed separately from the insert part 91 for remote operation and control of the insert part 91.

The endoscope 90 assembled in this way, because of incorporating the optical unit 1 according to the embodiment described herein, ensures that the optical unit 1 is of smaller size and well compatible with quick zoom change and the taking of moving images.

According to the embodiment described herein, there is an optical unit 1 provided, which includes a tubular fixed part 2 with a given axis C as center, a front frame part 4 that holds a front lens group Gf in place and is attached to an object side of the fixed part 2 with the axis C as center, a back frame part 5 that holds a back lens group Gb in place and is attached to an image side of the fixed part 2 with the axis C as center, a movable part 3 that holds a moving lens group Gv in place and is located inside the fixed part 2 with the axis C as center, and a voice coil motor 10 that is capable of moving the movable part 3 relatively with respect to the fixed part 2 in a direction of the axis C by a coil 11 located in the fixed part 2 and a magnet 12 located in the movable part 3 and magnetically polarized in a direction orthogonal to the axis C, wherein at least a part of the movable part 3 is included in a portion of the front frame part 4 projected in the axis C direction. It is thus possible to reduce the size and weight of the optical unit 1 in the diametrical direction and move the movable part 3 rapidly.

In the optical unit 1 according to one embodiment described herein, at least a part of the magnet 12 is included in the portion of the front frame part 4 projected in the axis C direction. It is thus possible to further reduce the size and weight of the optical unit 1 in the diametrical direction and move the movable part 3 more rapidly.

In the optical unit 1 according to one embodiment described herein, at least a part of the coil 12 is included in the portion of the front frame part 4 projected in the axis C direction. It is thus possible to further reduce the size and weight of the optical unit 1 in the diametrical direction and move the movable part 3 more rapidly.

In the optical unit 1 according to one embodiment described herein, the coil 12 is entirely included in the portion of the front frame part 4 projected in the axis C direction. It is thus possible to further reduce the size and weight of the optical unit 1 in the diametrical direction and move the movable part 3 more rapidly.

In the optical unit 1 according to one embodiment described herein, at least a part of the front frame part 4 or at least a part of the back frame part 5 is inserted on the inner circumference side of the movable part 3. It is thus possible to reduce the size and weight of the optical unit 1 in the axis C direction and move the movable part 3 rapidly.

In the optical unit 1 according to one embodiment described herein, a plurality of magnets 12 are located symmetrically with respect to the axis C. It is thus possible to boost the driving force of the voice coil motor 10 up enough for unerring movement of the movable part 3.

In the optical unit 1 according to one embodiment described herein, the magnet 12 includes a set of first magnets 12a and a set of second magnets 12b that are adjacent to each other in the axis C direction; the set of first magnets 12a has the same direction of magnetic polarization, and the set of second magnets 12b has the same direction of magnetic polarization; the magnetic polarization of the first magnets 12a and the magnetic polarization of the second magnets 12b adjacent to each other are in opposite directions; the coil 11 includes a first coil 11a opposite to the set of first magnets 12a and a second coil 11b opposite to the set of second magnets 12b; and the first coil 11a and the second coil 11b are reversed in a winding direction. It is thus possible to further boost the driving force of the voice coil motor 10 up enough for unerring movement of the movable part 3.

In the optical unit 1 according to one embodiment of the invention, the first magnet 12a and the second magnet 12b that are adjacent to each other are spaced away in the axis C direction. The mutual magnetic fields don't interfere with each other. It is prevented that the density of a magnetic flux coming in the coil opposite to each magnet decrease. It is thus possible to boost up the driving force of the voice coil motor 10 and reduce the size and weight of the optical unit 1, making sure unerring movement of the movable part 3.

The endoscope 90 according to one embodiment of the invention includes the aforesaid optical unit 1. It is thus possible to achieve size reductions, permit for rapid zoom change, and be well compatible with taking of moving images.

It is here to be appreciated that the invention is in no sense limited to such embodiments as described above. While the explanation of some embodiments embraces numerous specific details for illustration, it would be obvious to those skilled in the art that diverse variations or modifications made thereto are included within the scope of the invention. In other words, illustrative embodiments of the invention are described without excluding generality from the claimed inventions and imposing any limitation thereon.

REFERENCE SIGNS LIST

1: Optical unit
2: Fixed part
3: Movable part
4: Front frame part
5: Back frame part
10: Voice coil motor
11: Coil
12: Magnet

The invention claimed is:

1. An optical unit comprising:
    a tubular fixed part with a given axis as center;
    a front frame part that holds a front lens group in place and is attached to an object side of the fixed part with the axis as center;
    a back frame part that holds a back lens group in place and is attached to an image side of the fixed part with the axis as center;
    a movable part that holds a moving lens group in place and is located inside the fixed part with the axis as center; and
    a voice coil motor that is capable of moving the movable part relatively with respect to the fixed part in a direction of the axis by a coil located in the fixed part and a magnet located in the movable part and magnetically polarized in a direction orthogonal to the axis,
    wherein:
    at least a part of the movable part is included in a portion of the front frame part projected in the axis direction, and
    at least a part of the front frame part is inserted on an inner circumference side of the movable part.

2. An optical unit according to claim 1,
wherein at least a part of the magnet is included in the portion of the front frame part projected in the axis direction.

3. An optical unit according to claim 2,
wherein at least a part of the coil is included in the portion of the front frame part projected in the axis direction.

4. An optical unit according to claim 3,
wherein the coil is entirely included in the portion of the front frame part projected in the axis direction.

5. An optical unit according to claim 1,
wherein at least a part of the back frame part is inserted on an inner circumference side of the movable part.

6. An optical unit according to claim 1,
wherein a plurality of the magnets are located symmetrically with respect to the axis.

7. An optical unit according to claim 6, wherein:
the magnet includes a set of first magnets and a set of second magnets that are adjacent to each other in the axis direction,
the set of first magnets has the same direction of magnetic polarization, and the set of second magnets has the same direction of magnetic polarization,
the magnetic polarization of the first magnets and the magnetic polarization of the second magnets adjacent to the first magnets are in opposite directions,
the coil includes a first coil opposite to the set of first magnets and a second coil opposite to the set of second magnets,
and
the first coil and the second coil are reversed in a winding direction.

8. An optical unit according to claim 7,
wherein the first magnets and the second magnets adjacent to each other are spaced away in the axis direction.

9. An optical unit according to claim 1,
wherein a distance from the axis to a diametrically outer surface of the magnet is longer than a distance from the axis to an inner circumference surface of the fixed part.

10. An optical unit according to claim 9,
wherein:
the movable part includes a step on which the magnet is located,
and
the fixed part includes a lightened site on which the diametrically outer surface of the magnet is located.

11. An optical unit according to claim 1,
wherein an axial width of the coil is greater than an axial width of the magnet.

12. An endoscope comprising
an optical unit according to claim 1.

* * * * *